United States Patent
Ledgard

(10) Patent No.: US 9,481,688 B2
(45) Date of Patent: Nov. 1, 2016

(54) (THIENO[2,3-B][1,5]BENZOXAZEPIN-4-YL) PIPERAZIN-1-YL COMPOUNDS AS DUAL ACTIVITY H1 INVERSE AGONISTS/5-HT$_{2A}$ ANTAGONISTS

(75) Inventor: Andrew James Ledgard, Berkshire (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/125,320

(22) PCT Filed: Jul. 2, 2012

(86) PCT No.: PCT/US2012/045254
§ 371 (c)(1),
(2), (4) Date: Dec. 11, 2013

(87) PCT Pub. No.: WO2013/009517
PCT Pub. Date: Jan. 17, 2013

(65) Prior Publication Data
US 2014/0121199 A1    May 1, 2014

Related U.S. Application Data

(60) Provisional application No. 61/505,685, filed on Jul. 8, 2011.

(51) Int. Cl.
*A61K 31/553* (2006.01)
*C07D 498/04* (2006.01)
*A61K 45/06* (2006.01)

(52) U.S. Cl.
CPC ........... *C07D 498/04* (2013.01); *A61K 31/553* (2013.01); *A61K 45/06* (2013.01)

(58) Field of Classification Search
CPC ........................... A61K 31/553; C07D 498/04
USPC ........................................ 514/211.1; 540/548
See application file for complete search history.

(56) References Cited

FOREIGN PATENT DOCUMENTS

WO    2007/022068 A1    2/2007

*Primary Examiner* — Brenda Coleman
(74) *Attorney, Agent, or Firm* — R. Craig Tucker

(57) ABSTRACT

A dual H1/5-HT$_{2A}$ receptor antagonist of the formula:

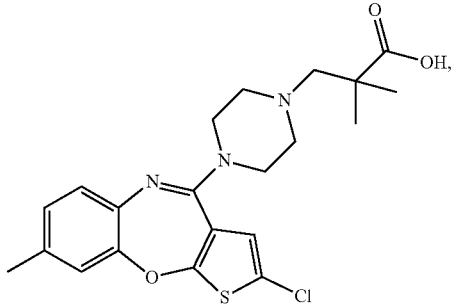

its uses, and methods for its preparation are described.

7 Claims, 3 Drawing Sheets

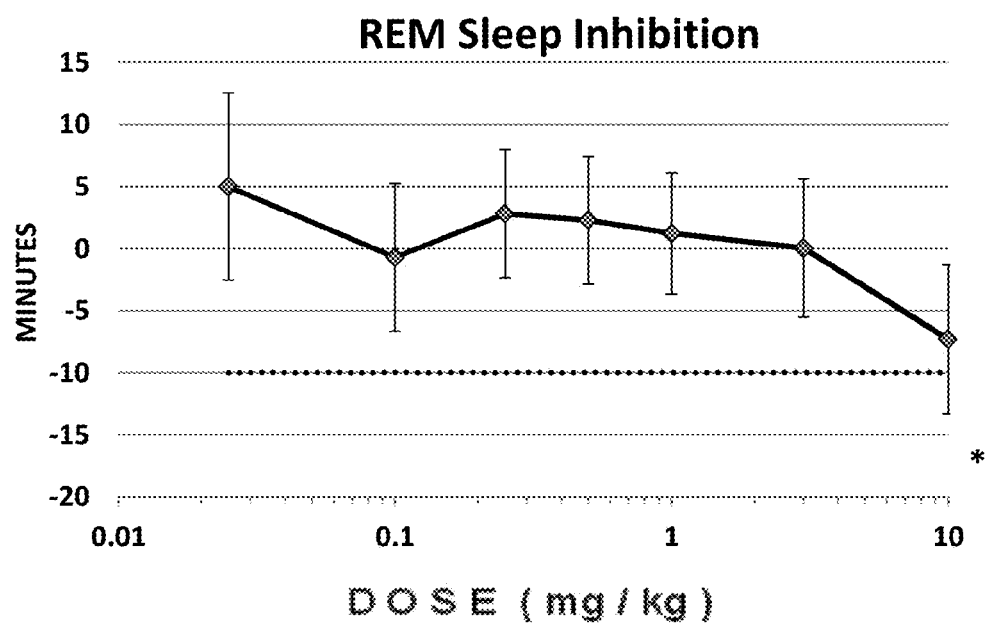
Figure 1. Dose response curve for change in cumulative time in REM sleep (Rapid Eye Movement sleep) as an indicator of REM inhibition for the compound of Example 3.

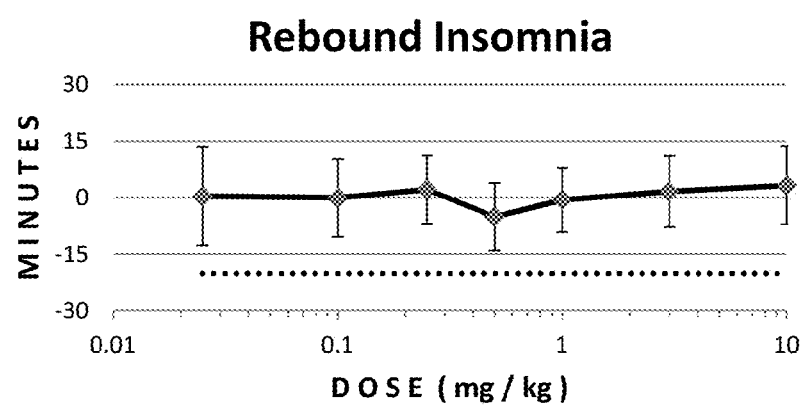
Figure 2. Dose response curve for the change in awake time following treatment with the compound of Example 3 as an indicator for rebound insomnia.

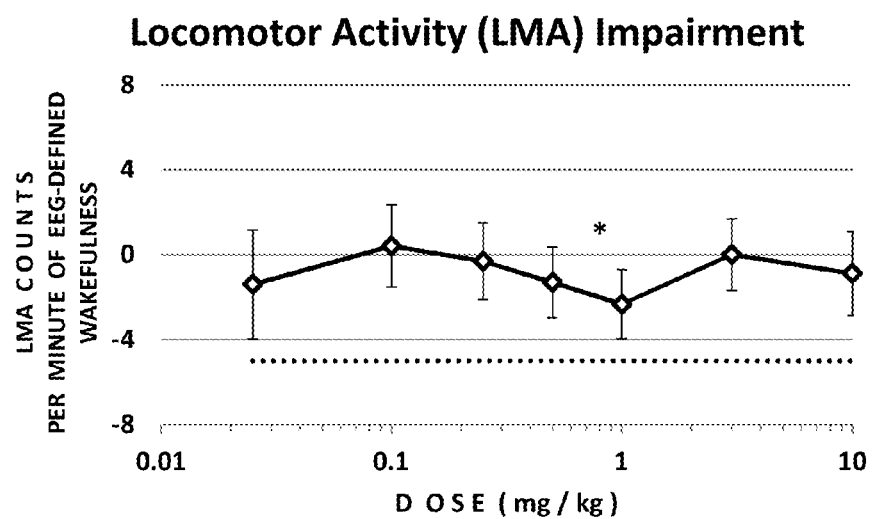
Figure 3. Dose response curve for the change in distances moved during periods of wakefulness during treatment with the compound of Example 3, demonstrating the compound does not inhibit or stimulate normal activity, vis a vis movement levels, during wakefulness.

(THIENO[2,3-B][1,5]BENZOXAZEPIN-4-YL) PIPERAZIN-1-YL COMPOUNDS AS DUAL ACTIVITY H1 INVERSE AGONISTS/5-HT$_{2A}$ ANTAGONISTS

This U.S. national stage application of International Application PCT/US2012/045254, filed Jul. 2, 2012, claims priority to U.S. provisional application Ser. No. 61/505,685, filed Jul. 8, 2011.

Histamine plays an important role in a variety of physiological processes through its interaction with at least four different G-protein coupled receptors, the H1-H4 receptors. In the CNS, H1 receptors play a key role in the sleep regulation cycle and H1 antagonists/inverse agonists are known to induce somnolence.

Likewise, serotonin plays important roles in a variety of physiological processes through its interaction with at least fourteen different G-protein coupled receptors. Modulation of 5-HT$_{2A}$ receptors in the CNS plays a key role in the sleep regulation cycle and 5-HT$_{2A}$ antagonists have been shown to improve slow wave sleep and sleep maintenance in patients with insomnia.

Compounds having H1 or 5-HT$_{2A}$ inverse agonist or antagonist activity have been used in the treatment of insomnia (e.g. doxepin and trazodone, respectively) and have exhibited significant pharmacological effects in animal sleep studies. However, no selective dual activity H1/5-HT$_{2A}$ inverse agonists/antagonists are currently commercially available.

WO 2007/022068 describes certain substituted (thieno[2,3-b][1,5]benzodiazepine-4-yl)piperazin-1-yl and (thieno[2,3-b][1,5]benzoxazepine-4-yl)piperazin-1-yl compounds for treating sleep disorders.

The present invention provides 3-[4-(2-chloro-8-methyl-thieno[2,3-b][1,5]benzoxazepin-4-yl)piperazin-1-yl]-2,2-dimethyl-propanoic acid and pharmaceutically acceptable salts thereof, having high inverse agonist potency for the H1 receptor, high antagonist potency for the 5-HT$_{2A}$ receptor, and good selectivity for these receptors, particularly as against other histamine receptors, serotonin receptors and other physiologically relevant receptors, particularly as against the 5-HT$_{2C}$ receptor, GABA$_A$ receptor, muscarinic receptors, dopaminergic receptors, adrenergic receptors, and the hERG channel. These compounds also demonstrate through animal models that they may be useful for the treatment of sleep disorders characterized by poor sleep maintenance. As such, the compounds are believed to be useful for the treatment of sleep disorders characterized by poor sleep latency or poor sleep maintenance or both, such as the treatment of insomnia, as for example chronic or transient primary insomnia, or chronic or transient secondary insomnia, or both. Examples of secondary insomnia include, but are not limited to insomnia associated with depressive disorders (e.g. major depressive disorder, dysthymia, and/or cyclothymia), insomnia associated with anxiety disorders (e.g. generalized anxiety disorder and/or social phobia), insomnia associated with pain (e.g. fibromyalgia, chronic bone or joint pain, such as associated with inflammatory arthritis or osteoarthritis, or diabetic neuropathic pain), insomnia associated with allergic reactions (e.g. allergic asthma, pruritus, rhinitis, congestion, etc.), insomnia associated lung or airway disorders (e.g. with obstructive sleep apnea, reactive airway disease, etc.), insomnia associated with psychiatric disorders, dementia, and/or neurodegenerative diseases, and/or insomnia associated with circadian rhythm sleep disorders (e.g. shift work sleep disorder, jet lag disorder, delayed sleep phase disorder, advanced phase sleep disorder, and non-24 hr. sleep-wake syndrome, etc.).

Further, the compounds of the present invention demonstrate potentiation of their effects on non-rapid eye movement sleep (NREM sleep) when coadministered with selective serotonin reuptake inhibitors.

The present invention provides a compound of Formula I

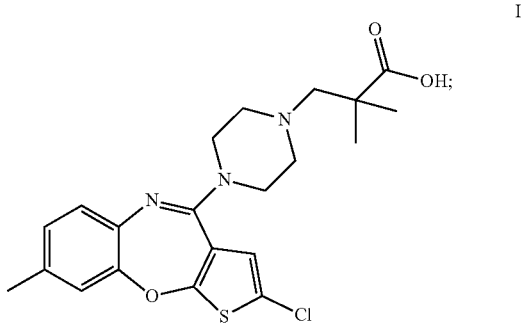 [SMILES: Cc1ccc2c(c1)Oc1sc(Cl)cc1C(N1CCN(CC(C)(C)C(=O)O)CC1)=N2]

or a pharmaceutically acceptable salt thereof. That is to say 3-[4-(2-chloro-8-methylthieno[2,3-b][1,5]benzoxazepin-4-yl)piperazin-1-yl]-2,2-dimethylpropanoic acid or a pharmaceutically acceptable salt thereof.

In another aspect of the invention there is provided a pharmaceutical composition comprising a compound of Formula I or a pharmaceutically acceptable salt thereof, in combination with at least one pharmaceutically acceptable carrier, diluent, or excipient. Furthermore, this aspect of the invention provides a pharmaceutical composition for treating insomnia, as for example insomnia characterized by prolonged sleep latency or poor sleep maintenance or both, as for example primary insomnia, jet lag, shift work sleep disorder, delayed sleep phase disorder, advanced phase sleep disorder, and/or non-24 hr. sleep-wake disorders, comprising a compound of Formula I or a pharmaceutically acceptable salt thereof, in combination with one or more pharmaceutically acceptable excipients, carriers, or diluents.

A further embodiment of this aspect of the invention provides a pharmaceutical composition comprising a compound according to Formula I, or pharmaceutically acceptable salt thereof, in combination with at least one pharmaceutically acceptable carrier, exciepient or diluent, and optionally other therapeutic ingredients. In a yet further embodiment of this aspect of the invention, the pharmaceutical composition further comprises a second therapeutic agent which is a serotonin reuptake inhibitor, as for example citalopram, paroxetine, fluoxetine and/or fluvoxetine.

The present invention also provides a method of treating insomnia, as for example insomnia characterized by prolonged sleep latency or poor sleep maintenance or both, as for example primary insomnia, jet lag, shift work sleep disorder, delayed sleep phase disorder, advanced phase sleep disorder, and/or non-24 hr. sleep-wake disorders, in a mammal comprising administering to a mammal in need of such treatment an effective amount of a compound of Formula I or a pharmaceutically acceptable salt thereof. In another embodiment of this aspect of the invention, the method further comprises administering in simultaneous, separate or sequential combination, a second therapeutic agent which is a serotonin reuptake inhibitor, as for example citalopram, paroxetine, fluoxetine and/or fluvoxetine. In one particular embodiment of these methods of treatment, the mammal is a human.

This invention also provides a compound of Formula I or a pharmaceutically acceptable salt thereof for use in therapy. Within this aspect, the invention provides a compound of Formula I, or a pharmaceutically acceptable salt thereof, for use in the treatment of insomnia. In further embodiments, the insomnia is characterized by prolonged sleep latency or poor sleep maintenance or both, as for example primary insomnia, jet lag, shift work sleep disorder, delayed sleep phase disorder, advanced phase sleep disorder, and/or non-24 hr. sleep-wake disorders. In another embodiment of this aspect, the invention provides a compound according to Formula I, or a pharmaceutically acceptable salt thereof, for use in simultaneous, separate or sequential combination with a serotonin reuptake inhibitor, as for example citalopram, paroxetine, fluoxetine and/or fluvoxetine, in the treatment of insomnia. One particular embodiment of this aspect of the inventions, the uses are in mammals, particular humans.

Another aspect of this invention provides the use of a compound of Formula I, or a pharmaceutically acceptable salt thereof, in the manufacture of a medicament for the treatment of insomnia, as for example primary insomnia characterized by prolonged sleep latency or poor sleep maintenance or both, as for example primary insomnia, jet lag, shift work sleep disorder, delayed sleep phase disorder, advanced phase sleep disorder, and/or non-24 hr. sleep-wake disorders. Another embodiment of this aspect of the invention provides the use of a compound of Formula I, or a pharmaceutically acceptable salt thereof, and a second therapeutic agent which is a serotonin reuptake inhibitor, as for example citalopram, paroxetine, fluoxetine and/or fluvoxetine, in the manufacture of a medicament for the treatment of insomnia, as for example, insomnia characterized by prolonged sleep latency and/or poor sleep maintenance, as for example primary insomnia, jet lag, shift work sleep disorder, delayed sleep phase disorder, advanced phase sleep disorder, and/or non-24 hr. sleep-wake disorders.

BRIEF DESCRIPTION OF FIGURES

FIG. 1 is a the dose response curve for the change in cumulative REM sleep time for the compound of Example 3, demonstrating the compound does not inhibit REM sleep.

FIG. 2 is a the dose response curve for the change in awake time following treatment with the compound of Example 3, demonstrating the compound does not result in rebound insomnia.

FIG. 3 is a the dose response curve for the change in distances moved during periods of wakefulness for the compound of Example 3, demonstrating the compound does not inhibit or stimulate normal activity, vis a vis movement levels, during wakefulness.

For clarity, the following numbering of the tricyclic ring structure will be used throughout the application:

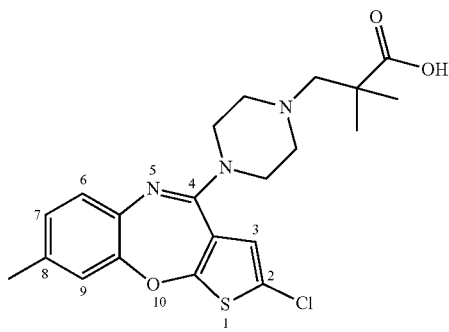 [SMILES: Cc1ccc2c(c1)Oc1sc(Cl)cc1C(N1CCN(CC(C)(C)C(=O)O)CC1)=N2]

The compound of this invention has basic and acidic moieties, and accordingly reacts with a number of organic and inorganic acids and bases to form pharmaceutically acceptable salts. Pharmaceutically acceptable salts of the compound of the present invention are contemplated within the scope of the present application. The term "pharmaceutically acceptable salt" as used herein, refers to any salt of a compound of the invention that is substantially non-toxic to living organisms. Such salts include those listed in *Journal of Pharmaceutical Science*, 66, 2-19 (1977), which are known to the skilled artisan.

Abbreviations used herein are defined as follows:

"DMEM" means Dulbecco's Minimum Eagle's Medium.

"DMSO" means dimethyl sulfoxide.

"EDTA" means ethylenediaminetetraacetic acid.

"FBS" means fetal bovine serum.

"HEPES" means 4-(2-hydroxyethyl)-1-piperazine ethanesulfonic acid.

"HPLC" means high pressure liquid chromatography.

"hr." means hours.

"$IC_{50}$" means the concentration at which 50% of the maximum inhibition is achieved.

"LC-MS" means HPLC-mass spectrography.

"MeOH" means methanol.

"min." means minutes.

"MS" means mass spectroscopy.

"MS (ES+)" means mass spectroscopy using electrospray ionization.

"NMR" means nuclear magnetic resonance.

"THF" means tetrahydrofuran.

General Chemistry

The compound of the present invention can be prepared according to the following synthetic examples.

Preparation 1. 2,5-dichlorothiophene-3-carbonyl chloride

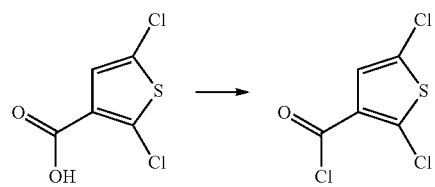 [SMILES: O=C(O)c1cc(Cl)sc1Cl ; O=C(Cl)c1cc(Cl)sc1Cl]

To a suspension of 2,5-dichloro-thiophene-3-carboxylic acid (49.7 g; 252.23 mmoles; 1.00 equiv) in dichloromethane (500 mL), add dimethylformamide (0.5 mL; 6.47 mmoles) followed by a solution of 2 M oxalyl chloride in dichloromethane (138.73 mL; 277.45 mmoles; 1.1 equiv) over 1.5 hr. (vent the evolved gas through a caustic solution). Stir the resulting clear solution at room temperature for 1 hr. until gas evolution has ceased and the reaction is complete by LCMS (quench a sample into 7 M $NH_3$/MeOH for reaction monitoring) MS (m/z): =195.9, 197.9 $(M+H)^+$ for corresponding primary amide. Evaporate to dryness to give the title intermediate as a brown oil (55 g, 252 mmol, quantitative).

Preparation 2. 2,5-dichloro-N-(2-hydroxy-4-methyl-phenyl)thiophene-3-carboxamide

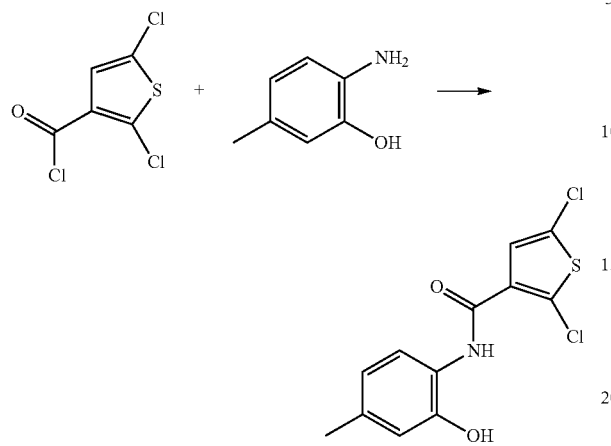

To a solution of 6-amino-m-cresol (34.14 g; 277.20 mmoles; 1.1 equiv) in THF (450 mL), add pyridine (40.76 mL; 504.00 mmoles; 2 equiv), followed by a solution of 2,5-dichlorothiophene-3-carbonyl chloride (54.30 g, 252 mmoles, 1.00 equiv) in THF (250 mL) over 30 min., using an ice-bath to maintain a temperature of 15-20° C. Stir the resulting thick mixture at room temperature for 1 hr. to give complete consumption of the aminophenol by LC-MS. Pour onto a mixture of 2 M aqueous HCl (500 ml) and ice (250 ml) with agitation. Collect the resulting beige solid by filtration, wash well with water, and dry in air. MS (m/z): =301.84, 303.94 (M+H)+. Dry in a vacuum oven at 40° C. over $P_2O_5$ overnight to give the title intermediate (84.5 g, assumed quantitative).

Preparation 3. 2-chloro-8-methyl-5H-thieno[2,3-b][1,5]benzoxazepin-4-one

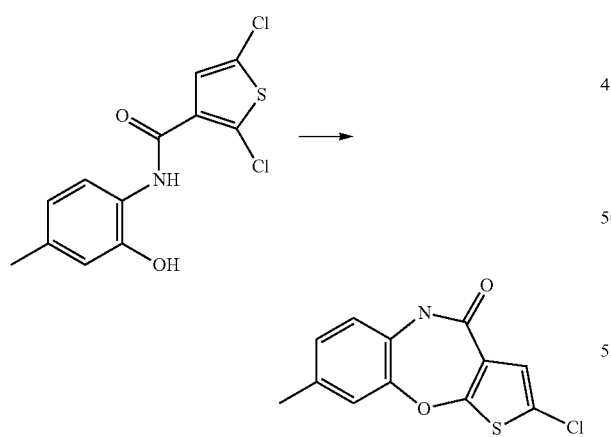

To a well-stirred suspension of 2,5-dichloro-N-(2-hydroxy-4-methyl-phenyl)thiophene-3-carboxamide (76.15 g; 252 mmoles; 1.00 equiv) in dimethyl sulfoxide (450 mL), add potassium carbonate (38.31 g; 277.20 mmoles; 1.1 equiv) and heat the mixture to 100-110° C. for 4.5 hr. to give essentially complete conversion by LCMS. Allow to cool to room temperature and slowly add to two separate beakers containing 1 M aqueous hydrochloric acid (500 ml), observ- ing gas evolution. Stir at room temperature for 0.5 hr. and collect the resulting dark grey solid by filtration. Wash sequentially with water, followed by a small amount of ethanol, followed by a small amount of diethyl ether. Dry in a vacuum oven at 45° C. overnight to give the title intermediate (58.5 g, 87%). MS (m/z): =265.99 (M+H)+.

Preparation 4. 2,4-dichloro-8-methyl-thieno[2,3-b][1,5]benzoxazepine

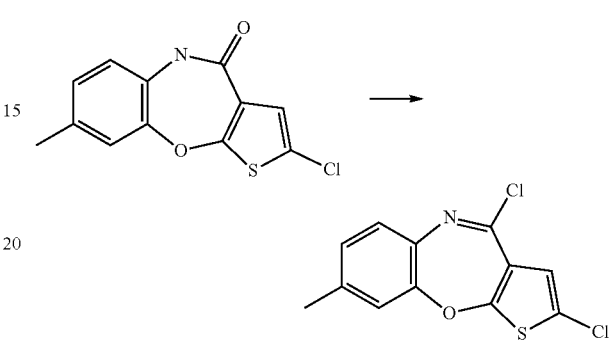

Charge a 1 L round bottom flask with methoxybenzene (225 mL, 5V), 2-chloro-8-methyl-5H-thieno[2,3-b][1,5]benzoxazepin-4-one (45 g; 169.4 mmoles; 1 equiv) and N,N-dimethylaniline (47.2 g; 389.5 mmoles; 2.3 equiv). Heat to 60° C. and add phosphoryl chloride (85.7 g; 558.9 mmols; 3.3 equiv) drop wise over 0.5 hr. Warm up to 100° C. and stir for 2 hr. until complete by TLC analysis. Cool to 40-60° C. and evaporate to obtain the title intermediate as a dark brown solid (123.1 g, 433.2 mmoles, 256% yield uncorrected by assay). MS (m/z): 283.8 (M+H).

Preparation 5. Methyl 3-[4-(2-chloro-8-methyl-thieno[2,3-b][1,5]benzoxazepin-4-yl)piperazin-1-yl]-2,2-dimethyl-propanoate

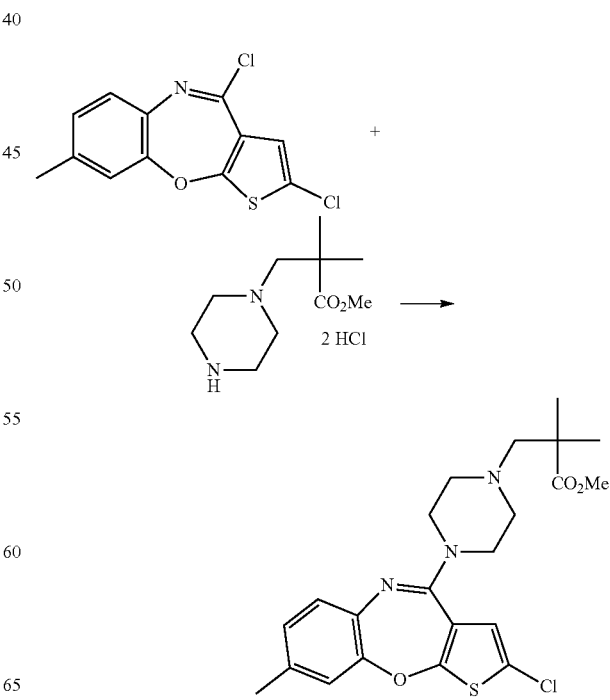

Charge a 1 L round bottom flask with 2,4-dichloro-8-methyl-thieno[2,3-b][1,5]benzoxazepine (121.1 g; 169.4 mmols; 1.0 equiv), followed by acetonitrile (600 mL, 12.5V), then potassium carbonate (119.4 g; 863.9 mmols) in one portion. Stir for 10-20 min. and then add methyl 2,2-dimethyl-3-(piperazin-1-yl)propanoate dihydrochloride (55.54 g; 203.3 mmoles; 1.2 equiv) in one portion. Heat to 80° C. and stir for 30 hr. Concentrate the mixture to dryness under vacuum, then charge ethyl acetate (1920 mL, 40V) and water (1920 mL, 40V) into the mixture. Stir, filter and then separate the water phase and extract with ethyl acetate (960 mL, 20V). Combine the organic phases and wash with water (960 mL×2) and brine (200 mL, 4V). Concentrate and purify by silica gel column (petroleum ether/ethyl acetate (0 to 10%)) to obtain the title intermediate as yellow solid (55.4 g, 123.7 mmoles, 95.8% purity, 73.0% yield uncorrected by assay). MS (m/z): 448.2 (M+H). $^1$H NMR (400 MHz, CDCl$_3$): δ7.03 (d, J=8.8 Hz, 1H), 6.91 (d, J=1.6 Hz, 1H), 6.81 (s, 1H), 6.50 (s, 1H), 3.67 (s, 3H), 3.47 (t, J=4.4 Hz, 4H), 2.58-2.54 (q, 6H), 2.28 (s, 3H), 1.19 (s, 6H).

EXAMPLE 1

3-[4-(2-Chloro-8-methyl-thieno[2,3-b][1,5]benzoxazepin-4-yl)piperazin-1-yl]-2,2-dimethyl-propanoic acid

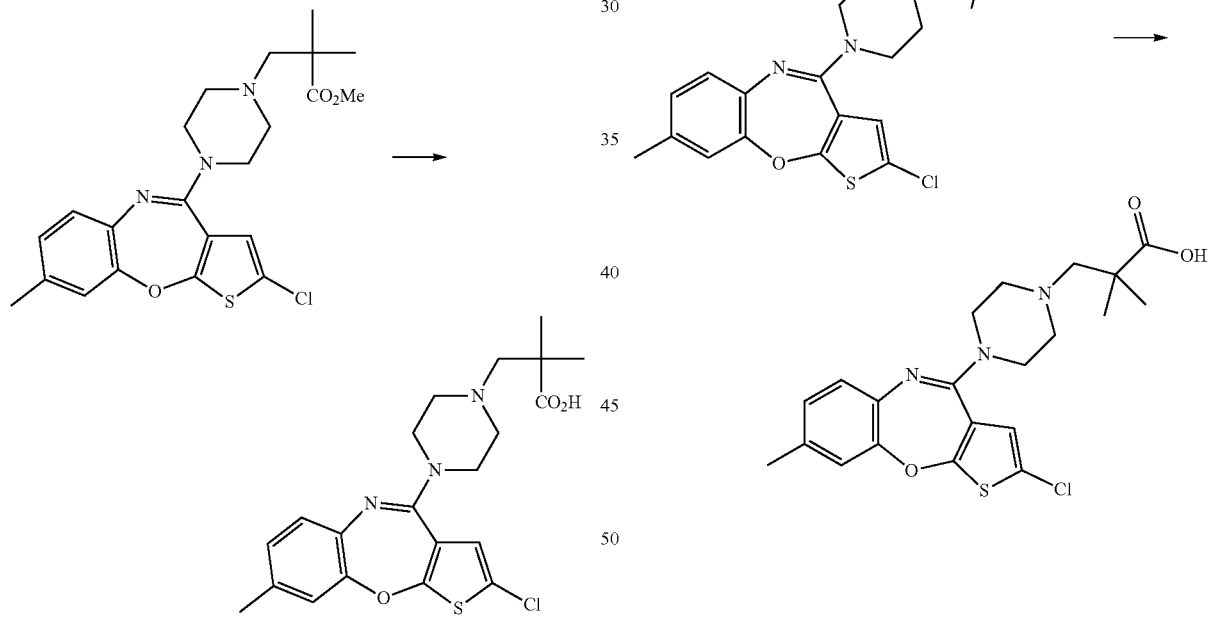

Charge a 2 L round bottom flask with methyl 3-[4-(2-chloro-8-methyl-thieno[2,3-b][1,5]benzoxazepin-4-yl)piperazin-1-yl]-2,2-dimethyl-propanoate (70.3 g; 156.9 mmoles; 1.0 equiv), isopropyl alcohol (469 mL; 6.67V) and water (469 mL; 6.67V). Then add sodium hydroxide (18.83 g; 470.8 mmoles; 3.0 equiv) and heat the mixture to 80° C. with stirring for 3 hr. Cool to 20° C. and neutralize to pH 7 with 5 M aqueous HCl. Evaporate most of the isopropyl alcohol then adjust the pH to 6-7 with 5 M aqueous HCl and concentrate to remove solvents. Charge ethyl acetate (2800 mL, 40V) and water (2800 mL, 40V) then stir for 30 min. before filtering to obtain crude product. Separate the water phase and extract with ethyl acetate (700 mL, 10V). Combine ethyl acetate layers and evaporate to obtain crude product. Charge the crude product and isopropyl alcohol (500 mL, 7V) into 1 L round bottom flask. Heat to 80° C. and stir for 1 hr., then cool to 20° C. slowly. Filter and wash the cake with isopropyl alcohol (70 mL, 1 V) to obtain the title compound as yellow solid (60.4 g; 138.6 mmoles; 99.3% purity, 88.3% yield corrected by assay). MS (m/z): 434.0 (M+H). $^1$H NMR (400 MHz, CDCl$_3$): δ7.01 (d, J=8.0 Hz, 1H), 6.94 (d, J=1.2 Hz, 1H), 6.92 (s, 1H), 6.83 (s, 1H), 3.64 (brs, 4H), 2.86 (brs, 4H), 2.60 (s, 2H), 2.19 (s, 3H), 1.26 (s, 6H). 13C NMR (400 MHz, CDCl$_3$): δ178.57, 161.10, 154.37, 152.00, 136.63, 135.64, 127.95, 127.14, 121.88, 121.20, 120.14, 118.58, 65.70, 54.46, 46.45, 41.54, 25.34, 20.70.

EXAMPLE 2

3-[4-(2-chloro-8-methyl-thieno[2,3-13][1,5]benzoxazepin-4-yl)piperazin-1-yl]-2,2-dimethyl-propanoic acid

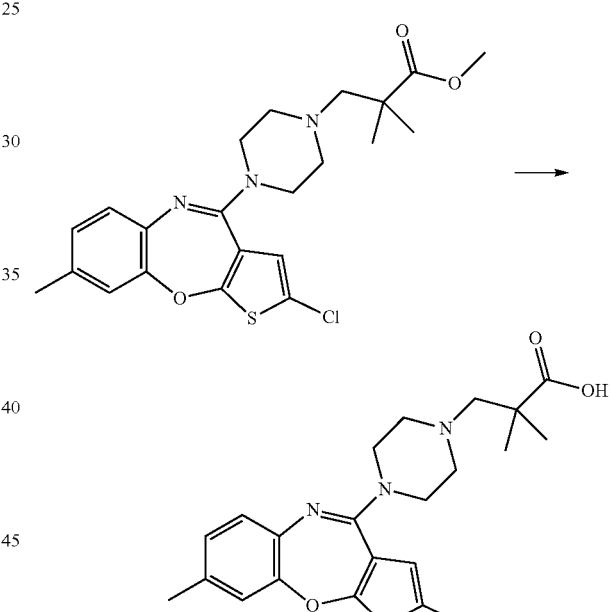

To a suspension of methyl 3-[4-(2-chloro-8-methyl-thieno [2,3-b][1,5]benzoxazepin-4-yl)piperazin-1-yl]-2,2-dimethyl-propanoate (22.5 g; 50.23 mmoles; 1.00 equiv) in a mixture of isopropyl alcohol (150 mL; 1.96 moles) and water (150 mL) add sodium hydroxide (6.03 g; 150.68 mmoles; 3 equiv) and heat the mixture at 80° C. (oilbath) for 2.5 hr. to give complete conversion by LC-MS. Allow to cool and neutralize to pH 7 with 5 M aqueous HCl. Evaporate most of the isopropyl alcohol to give a fine precipitate. Readjust the pH with 5 M aqueous HCl to pH 7. Stand the flask in a refrigerator for 0.5 hr. then collect the pale-yellow solid by filtration, washing with water. Dry in a vacuum oven at 45° C. over P$_2$O$_5$ overnight to give the title compound (20.6 g, 95%). MS (m/z): =434.1 (M+H)$^+$.

EXAMPLE 3

3-[4-(2-chloro-8-methyl-thieno[2,3-b][1,5]benzoxazepin-4-yl)piperazin-1-yl]-2,2-dimethyl-propanoic acid dihydrochloride

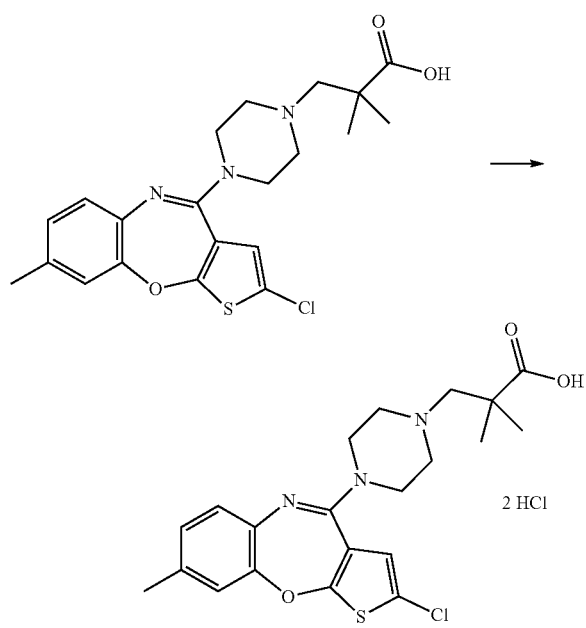

Slurry 3-[4-(2-chloro-8-methyl-thieno[2,3-b][1,5]benzoxazepin-4-yl)piperazin-1-yl]-2,2-dimethyl-propanoic acid (5.8 g; 13.3 mmol) in a small amount of acetonitrile, then add 4 M dioxane solution of hydrogen chloride (14.06 g; 53.57 mmoles; 4 equiv) and evaporate the resulting solution to dryness. Triturate with a small amount of diethyl ether, collect by filtration and dry in a vacuum oven to give the title compound (4.74 g, 70%); MS (m/z): =434.1 (M+H)+.

Additional Purification of the Dihydrochloride Salt

Take 3-[4-(2-chloro-8-methyl-thieno[2,3-b][1,5]benzoxazepin-4-yl)piperazin-1-yl]-2,2-dimethyl-propanoic acid dihydrochloride (7.5 g; 14.80 mmoles; 1.00 equiv) and heat in ethanol (150 ml) with sonication until a complete mixture is obtained. Evaporate to dryness. Triturate with a small amount of diethyl ether and collect the beige solid by filtration. Grind to a fine powder and dry in a vacuum oven at 50° C. over 2 nights to give the title compound (7.14 g, 95%). MS (m/z): =434.1 (M+H)$^+$.

Literature data (Morairty S R, Hedley L, Flores J, Martin R, Kilduff T S. (2008) *Selective 5-HT$_{2A}$ and 5-HT$_6$ receptor antagonists promote sleep in rats. Sleep* 31, 34-44; and Barbier, A. J., and Bradbury, M. J., *Histaminergic Control of Sleep-Wake Cycles: Recent Therapeutic Advances for Sleep and Wake Disorders*, CNS & Neurological Disorders—Drug Targets, vol 6, pg. 31-43 (2007)) and data generated in non-clinical animal studies support a role for dual activity H1 inverse agonists/5-HT$_{2A}$ antagonists in the treatment of insomnia and in the symptomatic treatment of insomnia associated with other disorders such as depressive disorders, anxiety disorders, pain, allergies, lung or airway disorders, psychiatric disorders, dementia, and/or neurodegenerative diseases, and/or circadian rhythm sleep disorders. Specifically it is found that certain dual activity H1 inverse agonists/5-HT$_{2A}$ antagonists are effective in increasing total sleep time using EEG monitored rodents without disproportionate or clinically relevant hypoactivity, decrease in REM sleep, or hypersomnolence.

To further demonstrate the characteristics of the present compounds, they may be run in the following in vitro and in vivo assays:

In Vitro Binding and Activity Assays:

H1 Competition Binding Assay

[$^3$H]-Pyrilamine binding experiments are carried out in SPA (scintillation proximity assay) 96-well format. Membranes used in this assay are prepared from HEK-293 cells stably expressing recombinant H1 receptor (human). The incubation is initiated by the addition of a mixture of WGA PVT SPA beads (1 mg/well, Perkin Elmer (MA, USA) RPNQ0001) and 3 μg membranes to assay buffer (67 mM Tris; pH 7.6) containing 3.5 nM [$^3$H]-Pyrilamine and varying concentrations of the test compound (10 point concentration response curves). Non-specific binding is determined in the presence of 10 μM Triprolidine. Samples are incubated for 4 hr. at room temperature (22° C.) and then read in a Microbeta Trilux.

5-HT$_{2A}$ Competition Binding Assay

[$^3$H]-Ketanserin binding experiments are carried out in SPA 96-well format. Membranes used in this assay are prepared from AV-12 cells stably expressing recombinant 5-HT$_{2A}$ receptor (human). The incubation is initiated by the addition of a mixture of WGA YSi SPA beads (1 mg/well, Perkin Elmer (MA, USA), RPNQ0011) and 2 μg membranes to assay buffer (67 mM Tris, 0.5 mM EDTA; pH 7.6) containing 3.1 nM [$^3$H]-Ketanserin and varying concentrations of the test compound (10 point concentration response curves). Non-specific binding is determined in the presence of 20 μM 1-(1-Naphthyl) piperazine. Samples are incubated for 4 hr. at room temperature (22° C.) and then read in a Microbeta Trilux.

5-HT$_{2C}$ Competition Binding Assay

[$^{125}$I]-(±)DOI binding experiments are carried out in SPA 96-well format. Membranes used in this assay are prepared from AV-12 cells stably expressing recombinant 5-HT$_{2C}$ receptor (human). The incubation is initiated by the addition of a mixture of WGA PVT SPA beads (0.5 mg/well, Perkin Elmer (MA, USA), RPNQ0001) and 2.5 μg membranes to assay buffer (50 mM Tris-HCl, 10 mM MgCl$_2$, 0.5 mM EDTA, 10 μM pargyline, 0.1% ascorbic acid, pH7.4) containing 0.2 nM [[$^{125}$I]-(±)DOI and varying concentrations of the test compound (10 point concentration response curves). Non-specific binding is determined in the presence of 20 μM 1-(1-Naphthyl) piperazine. Samples are incubated for 4 hr. at room temperature (22° C.) and then read in a Microbeta Trilux.

Binding Data Analysis

Curves are evaluated using a 4-parameter logistic nonlinear equation to obtain the concentration of competitor causing 50% inhibition of radioligand binding (IC$_{50}$). Equilibrium dissociation constants (K$_i$) are calculated according to the equation K$_i$=IC$_{50}$/(1+L/K$_d$), where L equals the concentration of radioligand used in the experiment and K$_d$ equals the equilibrium dissociation constant of the radioligand for the receptor, determined from standard saturation analysis or homologous competition experiments. Reported values for K$_i$, where n values are indicated, are shown as geometric mean±the standard error of the mean (SEM), with the number of replicate determinations indicated by n. Geometric means are calculated by the equation GeoMean=10^ (Average (log K$_i$ 1+log K$_i$ 2+ . . . log K$_i$ n)/sqrt n).

GABA$_A$ Antagonism Using Native Receptors in Primary Neuronal Cultures

Activity of compounds on native GABA$_A$ receptors is evaluated by monitoring calcium fluxes using a 96 well format FLIPR® system (Fluorometric Imaging Plate Reader (FLIPR®, Molecular Devices). Briefly, cortical embryonic neurons are dissociated from E18 rat embryos and plated at optimum density into black-walled, transparent bottom poly-D-lysine coated 96-well FLIPR® plates. After loading the cells with a calcium sensitive dye (Fluo4-AM, Molecular Devices), the cells are bathed in a solution containing low chloride (chloride replaced by gluconate). Under these conditions activation of GABA$_A$ receptors causes an efflux of chloride ions (in the direction of the chemical gradient), which results in membrane depolarization and consequently activation of voltage gated calcium channels (VGCCs). Calcium influx through VGCCs is recorded and analysed offline using the FLIPR® system. For a pharmacological validation of the assay, concentration response curves (CRC) are recorded for the standard agonist (GABA) and standard antagonist (Gabazine). Any effects are determined in CRC mode against a fixed concentration of agonist GABA at 10 μM (equivalent to an EC$_{90}$ GABA response).

Methods:

The antagonist effects of compounds are quantified using 10-point dose response curves by comparing the peak fluorescent responses to the agonist GABA in the presence and absence of compound. The assay window is defined as the maximal response obtained by GABA at its predetermined EC$_{90}$ concentration minus the response obtained by a fully inhibiting concentration of gabazine (50 μM). Antagonist effects are calculated as a percent of the assay window. All data are calculated as relative IC$_{50}$ values using a four-parameter logistic curve fitting program (Prism Graphpad® 3.01). Antagonist potencies for all compounds are compared to gabazine with three replicates in each assay run.

Further, the compounds of the invention may be tested in binding assays and functional activity assays by well known methods for other physiologically important receptors such as, but not limited to, the hERG channel, other serotonin receptors (specifically 5-HT$_{1B}$, 5-HT$_{1D}$, receptors, lack of agonist activity at 5-HT$_{2B}$ receptors, 5-HT$_{2C}$, 5-HT$_5$, 5-HT$_6$, and 5-HT$_7$ receptors), dopaminergic receptors (specifically D1, D2, and D3), GABA$_A$ receptors, adrenergic receptors and monoamine transporters.

The compounds of examples 1 and 13 are tested essentially as described above and are found to have activity profiles as shown in Table 1.

TABLE 1

Selectivity data

| | Example 1 | Example 3 |
|---|---|---|
| H1 K$_i$ (nM) | 20.6 | 58.8 |
| 5-HT$_{2A}$ K$_i$ (nM) | 3.37 | 7.01 |
| 5-HT$_{2B}$ K$_i$ (nM) | | 121 |
| 5-HT$_{2B}$ Agonist EC$_{50}$ (nM) | — | >10,000 |
| 5-HT$_{2B}$ Antagonist K$_b$ (nM) | | 78.6 |
| 5-HT$_{2C}$ K$_i$ (nM) | 137 | 328 |
| GABA$_A$ IC$_{50}$ (μM) | | >100 |
| hERG Channel (μM) | | >100 |
| Dopamine D$_1$ K$_i$ (nM) | | 592 |
| Dopamine D$_2$ K$_i$ (nM) | 2780 | >4570 |
| Dopamine D$_3$ K$_i$ (nM) | >5510 | >5680 |
| 5-HT$_{1B}$ K$_i$ (nM) | | >5580 |
| 5-HT$_{1D}$ K$_i$ (nM) | | >3980 |
| 5-HT$_5$ K$_i$ (nM) | | >8810 |
| 5-HT$_6$ K$_i$ (nM) | | >5830 |
| 5-HT$_7$ K$_i$ (nM) | | >2060 |
| Adrenergic alpha$_{1A}$ K$_i$ (nM) | | >10200 |
| Adrenergic alpha$_{1B}$ K$_i$ (nM) | | >14700 |
| Adrenergic alpha$_{2A}$ K$_i$ (nM) | | >8990 |
| Adrenergic alpha$_{2B}$ K$_i$ (nM) | | >5760 |
| Adrenergic alpha$_{2C}$ K$_i$ (nM) | | >4230 |
| Serotonin Transporter | | >661 |
| Norepinephrine Transport | | >696 |
| Dopamine Transporter | | >871 |

Therefore, physiologically relevant doses of the compounds of the invention are expected to provide substantial inhibition of H1 and 5-HT$_{2A}$ receptors in vivo, while not substantially interacting with other physiologically relevant receptors, and thus are expected to provide the desired pharmacology while avoiding undesired effects associated with off-target activity. Such undesired effects include, but are not limited to the following: 5-HT$_{2C}$ antagonist activity associated with treatment emergent weight gain, 5-HT$_{2B}$ agonist activity associated with valvulopathy, hERG channel modulation associated with QT prolongation, and GABA$_A$ antagonist activity associated with seizure activity. Furthermore, interference with sleep/wake physiology is avoided by the selectivity over dopamine receptors, other serotonin receptors, adrenergic receptors, and monoamine transporters.

5-HT$_{2A}$ Receptor Occupancy:

Receptor occupancy is assayed to demonstrate antagonist/inverse agonist activity at the 5-HT$_{2A}$ Receptor in vivo. Briefly, male Sprague-Dawley rats (Harlan Sprague-Dawley, Indianapolis, Ind.) weighing approximately 230-280 grams are given ad lib access to food and water until the beginning of the 3-hr. experimental protocol. 1 mg/kg ketanserin (non-selective 5-HT$_{2A}$ antagonist) is used as a positive control to establish assay validity. Test compounds or control are administered by oral gavage in a vehicle comprised of 20% hydroxypropyl beta-cyclodextrin. MDL 100907 ((R)-(+)-α-(2,3-Dimethoxyphenyl)-1-[2-(4-fluorophenyl)ethyl]-4-piperidinemethanol), a selective 5-HT$_{2A}$ antagonist, is used as a tracer. MDL 100907 is suspended in water with 5 μl dilute lactic acid (1 mg/ml), diluted to 6 μg/ml with saline, and administered in a volume of 1 mL/kg intravenously via the lateral tail vein to yield a tracer dose of 3 μg/kg. Rats are administered test compound, ketanserin, or vehicle (N=4), followed 1 hr. later with an intravenous, 3 μg/kg tracer dose of MDL 100907. It is at the time of tracer administration that receptor occupancy (RO) is considered to be measured. Fifteen min. after tracer administration, rats are sacrificed by cervical dislocation. Plasma samples are collected and samples of the frontal cortex and cerebellum are removed. The level of MDL 100907 tracer is measured in each cortical and cerebellar sample. RO is calculated using the well-established ratio method which employs a region of high receptor density representative of total binding (frontal cortex) normalized by an area without or with very low levels of receptor (cerebellum). This region, referred to as the null region, represents nonspecific binding of the ligand probe. Vehicle ratio of the tracer levels in cortex relative to cerebellum represents 0% occupancy. A ratio of 1 represents 100% occupancy and is achieved when all specific binding to the 5-HT$_{2A}$ receptor of the MDL 100907 tracer is blocked. The intermediate ratios of cortical to cerebellar tracer from the test compound pretreated group are interpolated linearly between the ratio of tracer levels in the vehicle-treated animals (0% occupancy) and a ratio of 1 (100% occupancy) in order to determine the percent 5-HT$_{2A}$ RO.

MDL 100907 Analysis:

Cortex and cerebellar samples are weighed and placed in conical centrifuge tubes on ice. Four volumes (w/v) of acetonitrile containing 0.1% formic acid is added to each tube. The samples are then homogenized and centrifuged at 14,000 RPM (21,920×g) for 16 min. Supernatant is diluted by adding 100-900 µL sterile water in HPLC injection vials for LC/MS/MS analysis. Analysis of MDL 100907 is carried out using an Agilent model 1200 HPLC (Agilent Technologies, Palo Alto, Calif.) and an API 4000 mass spectrometer. The chromatographic separation is on a 2.1×50 mm C18 column (Agilent part number 971700-907) with a mobile phase consisting of 60% acetonitrile in water with an overall 0.1% formic acid content. Detection of MDL 100907 is accomplished by monitoring the precursor to product ion transition with a mass to charge ratio (m/z) of 374.2 to 123.0. Standards are prepared by adding known quantities of analyte to brain tissue samples from non-treated rats and processing as described above.

Statistical Methods:

Curves for each study are fitted to a 4 parameter logistic function with the bottom fixed at 0% using JMP® version 8.0 (SAS Institute Inc, Cary N.C.) and the absolute ED$_{50}$ is calculated by the software. Values are given as means, standard errors and 95% confidence intervals. The compound of Example 3 is tested essentially as described and is found to achieve high 5-HT$_{2A}$ receptor occupancy with an ED$_{50}$ of 0.09 mg/kg.

H1 Inverse Agonism:

To determine the inverse agonist nature of compounds of the present invention, their effects on the levels of Myo-Inositol 1 phosphate (IP1) in HEK293 cells transfected with the human recombinant H1 receptor (HEK293/hm H1 clone R-40) are measured. Briefly, HEK293/hm H1 cells (clone R-40) are grown to ~90% confluency (3:1 DMEM/F12, 5% FBS, 20 mM HEPES, G418 500 µg/ml, 1% Pen/Strep/Glutamine) and harvested on the day of the assay using 1× Trypsin/EDTA (PAA Pasching, Austria L11-003). 35 µl cells (300K) are seeded into 96W half area white solid bottom plates (Corning, UK 3688) in stimulation buffer (NaCl 146 mM, CaCl$_2$ 1 mM, KCl 4.2 mM, MgCl$_2$ 0.5 mM, Glucose 5.5 mM, HEPES 10 mM and LiCl 50 mM). Test compounds are initially dissolved in 100% DMSO at 100× final concentration. These are further diluted to ×2 final assay concentration in stimulation buffer and 35 µl of this solution is then added to the cells in the assay plate. Cells plus compound are incubated for 1 hr. 30 min. at 37° C./5% CO$_2$ before addition of 15 µl of each of the HTRF IP1 detection kit reagents (CisBio 62P1APEC). The cell plate is incubated for a further hour at room temperature before measuring IP1 accumulation (Envision plate reader, Perkin Elmer). IP1 accumulation (nM) is calculated by extrapolation from the standard IP1 curve run on the day of the assay. Negative efficacy values are expressed relative to the positive control Tripelennamine (10 µM, Sigma, UK P5514). Compound 3 is tested essentially as described and is found to fully suppress constitutive activity (105% at 1 µM and 85% at 10 µM (n=2)).

Inhibition of DOI Induced Headshake Activity:

The in vivo 5-HT$_{2A}$ receptor antagonist activity of the compound of the present invention is further demonstrated by its ability to block head shaking activity induced by the 5-HT$_{2A}$ receptor agonist 2,5-dimethoxy-4-iodoamphetamine (DOI). (see for example Bartoszyk G D, van Amsterdam C, Böttcher H, Seyfried C A. EMD 281014, a new selective serotonin 5-HT2A receptor antagonist. *Eur J Pharmacol.* 2003 473: 229-230.) Briefly, male C57BL/6J mice (20-25 g, Charles River) are housed in standard housing conditions (32 mice in a large IVC cage, 07.00 to 19.00 light phase, constant temperature (19-23° C.) and humidity (50%+/−10), ad lib food and water). Mice received either vehicle (0.25% Methyl cellulose), DOI (3 mg/kg in saline) or test compound at 10 mg/kg PO plus DOI (3 mg/kg in saline). Test compounds are individually evaluated in groups of four per experiment with n=4 for each compound, together with vehicle and DOI+vehicle (n=8). After a test compound pre-treatment time of 60 min. the mice receive either vehicle (saline) or 3 mg/kg DOI dosed subcutaneously, and are then placed into clear perspex observation chambers. Five min. after DOI or vehicle administration the number of visually scored head shakes exhibited by each individual mouse is counted for 15 min. The data is analyzed using an ANOVA and post-hoc Dunnet's Test. The compound of example 3 is tested essentially as described and is found to inhibit the DOI induced headshake response at 100% at 10 mg/kg.

Sleep and Behavioral Monitoring in Rats:

The compound of the present invention is tested in rats for its ability to increase the amount of sleep or decrease sleep interruption or both without undesired effects such as inhibition of REM sleep, waking motor impairment, and/or rebound insomnia. Test animals are continuously monitored by electro-encephalograms (EEG), electromyograms (EMG), and motion to measure cumulative nonREM sleep, cumulative total sleep, average sleep bout duration, longest sleep bout duration, rebound insomnia, REM sleep inhibition and locomotor activity intensity during wakefulness. Methods for such studies are known in the art (see for example methods described in Edgar D M, Seidel W F. Modafinil induces wakefulness without intensifying motor activity or subsequent rebound hypersomnolence in the rat. *J Pharmacology & Experimental Therapeutics* 1997; 283: 757-769; van Gelder R N, Edgar D M, Dement W C. Real-time automated sleep scoring: validation of a microcomputer-based system for mice. *Sleep* 1991, 14: 48-55; and Gross B A, Walsh C M, Turakhia A A, Booth V, Mashour G A, Poe G R. Open-source logic-based automated sleep scoring software using electrophysiological recordings in rats. *J Neurosci Methods.* 2009; 184(1):10-8.) Studies are conducted as follows:

Animal Preparation.

Adult, male Wistar rats (approximately 270-300 g at time of surgery) are surgically fitted for chronic recording of EEG, EMG, and motion as follows: Rats are surgically prepared with a cranial implant consisting of four stainless steel screws for EEG recording (two frontal [3.9 mm anterior from bregma, and ±2.0 mm mediolaterally] and two occipital [6.4 mm posterior from bregma, ±5.5 mm mediolaterally]), and with two Teflon-coated stainless steel wires for EMG recording (positioned under the nuchal trapezoid muscles). All leads are soldered to a miniature connector (Microtech, Boothwyn, Pa.) prior to surgery. The implant assembly is affixed to the skull by the combination of the stainless steel EEG recording screws, cyanoacrylate applied between the implant connector and skull, and dental acrylic. Locomotor activity is monitored via a miniature transmitter (Minimitter PDT4000G, Philips Respironics, Bend, Oreg.) surgically placed into the abdomen. At least 3 weeks are allowed for recovery.

Recording Environment.

Each rat is housed individually within a microisolator cage modified with an inserted polycarbonate filter-top riser to allow more vertical headroom. A flexible cable that minimally restricts movement is connected at one end to a commutator a fixed to the cage top and at the other end to the animal's cranial implant. Each cage is located within separate, ventilated compartments of a stainless steel sleep-wake recording chamber. Food and water are available ad libitum and the ambient temperature is maintained at about 23±1° C. A 24-hr light-dark cycle (LD 12:12) using fluorescent light is maintained throughout the study. Relative humidity averages approximately 50%. Animals are undisturbed for at least 30 hrs before and after each treatment.

Study Design and Dosing.

The vehicle (placebo, methylcellulose 15 centipoise 0.25% in water) or one of the test compound dose levels is administered orally at 1 mL/kg pseudo-randomly such that no rat receives the same treatment twice, and no rat receives more than two of the 8 treatments in any one study. Each rat is removed from its cage for about a minute to be weighed and treated. At least 6 days "washout" period precede and follow each treatment.

Data Collection.

Sleep and wakefulness discrimination may be automated (e.g., Van Gelder et al. 1991 (above); Edgar et al. 1997 (above); Winrow C J, et al., *Neuropharmacology* 2010; 58(1):185-94; and Gross et al., 2009 (above). EEG is amplified and filtered (×10,000, bandpass 1-30 Hz), EMG is amplified and integrated (bandpass 10-100 Hz, RMS integration), and non-specific locomotor activity (LMA) is monitored simultaneously. Arousal states are classified in 10 second epochs as non-REM sleep, REM sleep, wakefulness, or theta-dominated wakefulness. Locomotor activity (LMA) is recorded as counts per minute and is detected by commerically available telemetry receivers (ER4000, Minimitter, Bend, Oreg.).

Statistical Analysis.

All animals having at least one outcome are included in the summary results (for example, we include appropriate data from an animal treatment for which telemetry data is usable but EEG data is not). The post-treatment observation period is divided into post-dosing intervals appropriate to each Outcome, where the time of dosing is defined as the start of Hour=0, and outcomes are summarized in the observation period by computing either the mean hourly or the cumulative value across each period (see legend of Table 1 for precise definition of each Outcome). Sleep bouts are analyzed on the log scale to stabilize the variation, all other variates are analyzed on the linear scale. Each outcome in each period is analyzed by analysis of covariance using treatment group and treatment date as factors and the corresponding pre-treatment interval, 24 hrs earlier, as the covariate. Adjusted means and the change from vehicle means and their corresponding standard errors are summarized for each treatment group. Outcomes analyzed on the log scale are back-transformed to report geometric means and mean ratio-to-vehicle results.

The compound of Examples 3 is tested essentially as described. The compound of Example 3 is found to significantly increase cumulative NREM sleep time and cumulative total sleep time without significant rebound insomnia, REM sleep inhibition or inhibition of locomotor intensity (LMI) at 3 mg/kg. (See sleep profile and locomotor activity intensity in Table 2, and FIGS. 1, 2, and 3.)

TABLE 2

Compound of Example 3.

| Dose (mg/kg PO) | Efficacy variables | | | Undesired effect variables | | |
|---|---|---|---|---|---|---|
| | N | Adj. Mean | SE | N | Adj. Mean | LCL |
| Cumulative NREM sleep | | | | Rebound Insomnia | | |
| 10 | 9 | 29.1 | 6.4 | 9 | −3.1 | −11.0 |
| 3 | 10 | 31.7 | 6.1 | 10 | 0.3 | −7.3 |
| 1 | 4 | 34.0 | 9.0 | 4 | 1.6 | −9.8 |
| 0.5 | 4 | 32.9 | 9.0 | 4 | −5.0 | −16.3 |
| 0.25 | 12 | 37.9 | 6.0 | 12 | −2.2 | −9.8 |
| 0.1 | 8 | 26.7 | 7.4 | 8 | −3.7 | −13.0 |
| 0.05 | 14 | 23.4 | 5.7 | 14 | 0.2 | −7.0 |
| 0.035 | 7 | 19.2 | 7.1 | 7 | 1.3 | −7.7 |
| 0.025 | 10 | 6.5 | 6.1 | 10 | 1.4 | −6.3 |
| Cumulative Total sleep | | | | REM inhibition | | |
| 10 | 9 | 26.5 | 7.1 | 9 | −9.4 | −3.8 |
| 3 | 10 | 29.7 | 6.8 | 10 | −4.6 | 0.7 |
| 1 | 4 | 33.6 | 10.1 | 4 | −0.1 | 7.8 |
| 0.5 | 4 | 30.9 | 10.1 | 4 | 0.4 | 8.2 |
| 0.25 | 12 | 38.9 | 6.7 | 12 | 2.0 | 7.2 |
| 0.1 | 8 | 28.7 | 8.3 | 8 | 4.9 | 11.4 |
| 0.05 | 14 | 25.3 | 6.5 | 14 | 4.2 | 9.2 |
| 0.035 | 7 | 18.9 | 8.0 | 7 | −1.8 | 4.4 |
| 0.025 | 10 | 7.7 | 6.9 | 10 | 0.5 | 5.8 |
| Average Sleep Bout | | | | Locomotor Activity Intensity | | |
| 10 | 9 | 2.0 | 0.2 | 9 | −1.9 | −0.1 |
| 3 | 10 | 2.0 | 0.2 | 10 | −3.1 | −1.3 |
| 1 | 4 | 1.7 | 0.3 | 4 | −1.6 | 0.9 |
| 0.5 | 4 | 1.8 | 0.3 | 4 | 0.6 | 3.1 |
| 0.25 | 12 | 2.1 | 0.2 | 10 | −0.7 | 1.1 |
| 0.1 | 8 | 1.7 | 0.2 | 8 | 0.1 | 2.3 |
| 0.05 | 14 | 1.6 | 0.2 | 10 | −0.3 | 1.6 |
| 0.035 | 7 | 1.3 | 0.2 | 6 | 0.2 | 2.4 |
| 0.025 | 10 | 1.2 | 0.1 | 9 | 0.2 | 2.1 |
| Longest Sleep Bout | | | | | | |
| 10 | 9 | 2.3 | 0.3 | | | |
| 3 | 10 | 2.7 | 0.3 | | | |
| 1 | 4 | 2.0 | 0.3 | | | |
| 0.5 | 4 | 2.2 | 0.4 | | | |
| 0.25 | 12 | 2.0 | 0.2 | | | |
| 0.1 | 8 | 1.5 | 0.2 | | | |
| 0.05 | 14 | 1.4 | 0.2 | | | |
| 0.035 | 7 | 1.1 | 0.2 | | | |
| 0.025 | 10 | 1.1 | 0.1 | | | |

Table 2. Outcome statistics: Abbreviations: N = sample size; Adj. Mean = adjusted group mean value relative to vehicle controls; SE = standard error of the mean; LCL = lower 95% confidence limit, NREM = non-REM, i.e., all sleep other than REM sleep. The parallel reference vehicle group sample size was N = 27.
Definitions and units—means are adjusted differences from vehicle controls:
Cumulative sleep: across the first 6 hr. post-treatment, in minutes ('Total sleep' denotes NREM sleep + REM sleep).
Average sleep bout: average of hourly-averaged sleep bouts, across the first 6 hr. post-treatment, expressed as n-fold increase over vehicle controls.
Longest sleep bout: the longest sleep bout in the first 6 hr. post-treatment, expressed as n-fold increase over vehicle controls.
Rebound insomnia: cumulative minutes of NREM + REM sleep during the first 3 hr. of the lights on period, i.e., $7^{th}$, $8^{th}$ and $9^{th}$ hours post-treatment.
REM inhibition: cumulative minutes of REM sleep during the first 12 hr. post-treatment.
Locomotor Activity (LMA) Intensity: expressed as LMA counts per minute of EEG-defined wakefulness, averaged across the first 6 hr. post-treatment.

Determining Efficacy.

The threshold efficacy for each of the four efficacy variables is calculated by plotting the increase in each variable relative to vehicle controls during the 6 hr. period after treatment against log(dose). The threshold efficacy for each variable is that dose, estimated by 4 parameter logistic nonlinear regression, which gives the defined efficacy threshold value; +30 min. of additional accumulated non-REM sleep, +25 min. of additional accumulated total sleep, 1.75× increase in average sleep bout duration, and 1.5× increase in longest sleep bout duration. The compound of example 3 is found to have threshold efficacious doses as shown in Table 3.

TABLE 3

| | Estimated efficacy dose (mg/kg) | 95% confidence interval (mg/kg) |
|---|---|---|
| NREM accumulation = 30 min. | 0.09 | 0.04-n.e.* |
| total sleep accumulation = 25 min. | 0.05 | 0.03-0.09 |
| longest sleep bout (1.75-fold increase) | 0.12 | 0.07-0.20 |
| average sleep bout (1.5-fold increase) | 0.04 | 0.03-0.06 |

*n.e. = not estimable, statistically.

Determining Undesired Effects.

Each 'undesired effect' outcome variable (see Table 2 legend for definitions), is plotted against log(dose)(See FIGS. 1, 2, and 3). The threshold value for REM inhibition is defined as a cumulative reduction of REM sleep of −10 min. The threshold value for rebound insomnia is defined as −20 min. The threshold value for reduced LMI is defined as −5 locomotor activity counts per minute of EEG-defined wakefulness. A significant undesired effect is defined to occur when the lower confidence limit goes below the threshold value at any dose at or below 10 times the average efficacious dose, and a dose response trend is evident for doses above the threshold efficacy dose. For the compound of Example 3, no undesired occurrences of REM inhibition, rebound insomnia, or reduction in LMI are observed at doses up to at least 1.2 mg/Kg (1.2 mg/Kg is 10 times the most conservative efficacy dose of 0.12 mg/kg [Table 3]). Negative values indicate REM inhibition, rebound insomnia and reduced LMI, respectively.

In further studies, the compounds of the present invention may be coadministered with selective serotonin reuptake inhibitors to demonstrate a potentiation of their effect on non-rapid eye movement sleep (NREM sleep) and sleep maintenance. The compound of Example 3 is coadministered with citalopram in rat sleep studies essentially as described above for the compound alone, and is found to significantly increase NREM sleep at significantly lower doses.

Plasma Clearance:

It is important in a compound useful for treating sleep disorders such as insomnia that it be adequately cleared from the body with a favorable rate of clearance to avoid unwanted effects such as prolonged somnolence beyond the desired sleep period, daytime sleepiness, impaired cognition after waking, etc. The present invention provides compounds with improved rates of clearance. Rate of clearance can be assayed essentially as described below.

Male Sprague Dawley rats (body weight range 250-320 g) with indwelling femoral arterial cannulae are obtained from Charles River, Wilmington, Mass. 01887, USA. Test compound is administered intravenously in solution (1 mL/kg) in 20% Captisol® in 22.5 mM phosphate buffer, pH 2, at a final drug concentration of 1.0 mg/mL (free base equivalents). Blood samples are obtained using the indwelling cannula over 24 hr. Samples of plasma are obtained by centrifugation and stored frozen (−20° C.), or on dry ice, prior to analysis.

Male Beagle dogs (body weight range 10-12 kg) are obtained from Marshall Bioresources, USA. Test compound is administered intravenously in solution (1 mL/kg) in 20% Captisol® in 22.5 mM phosphate buffer, pH 2, at a final drug concentration of 1.0 mg/mL (free base equivalents). Blood samples are obtained from the jugular vein over 24 hr. Samples of plasma are obtained by centrifugation and stored frozen (−20° C.) prior to analysis.

Frozen plasma samples are thawed to room temperature for bioanalysis of concentrations of test compound. A related internal standard compound in acetonitrile/methanol (1:1, v/v) is added to all samples of plasma (1:1, v/v). The samples are centrifuged to remove precipitated protein prior to analysis. The supernatants are analysed by injection and rapid gradient elution on a Javelin Betasil C18 column (20×2.1 mm cartridge, Mobile phase A: Water/1 M $NH_4HCO_3$, 2000:10 v/v, Mobile Phase B: MeOH/1 M $NH_4HCO_3$, 2000:10 v/v). The eluted analytes are detected by LC-MS-MS analysis using a Sciex API 4000 triple quadrupole mass spectrometer. Concentrations of compound are determined from standards prepared and analysed under identical conditions. Clearance is calculated using non-compartmental analysis in Watson 7.4, Thermo Fisher Scientific, Inc.

$$\text{Clearance} = \frac{\text{Dose}}{\text{Area under curve for plasma concentration/time}}$$

The compounds of Examples 1 and 3 are run essentially as described and are found to have favorable clearance profiles:

| | Clearance (mL/min./Kg) | |
|---|---|---|
| Example | Rat | Dog |
| 1 | 14.1 (+/−6.9, n = 3) | — |
| 3 | 14.5 (+/−1.4, n = 3) | 3.2(+/−0.7, n = 3) |

While it is possible to administer the compounds as employed in the methods of this invention directly without any formulation, the compounds are usually administered in the form of pharmaceutical compositions comprising the compound, or a pharmaceutically acceptable salt thereof, as an active ingredient and at least one pharmaceutically acceptable carrier, diluent and/or excipient. These compositions can be administered by a variety of routes including oral, sublingual, nasal, subcutaneous, intravenous, and intramuscular. Such pharmaceutical compositions and processes for preparing them are well known in the art. See, e.g., Remington: The Science and Practice of Pharmacy (University of the Sciences in Philadelphia, ed., $21^{st}$ ed., Lippincott Williams & Wilkins Co., 2005).

The compositions are preferably formulated in a unit dosage form, each dosage containing from about 0.1 to about 60 mg, more usually about 0.5 to about 30 mg, as for example between about 1 and about 10 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds of Formula I are generally effective over a wide dosage range. For example, dosages per day normally fall within the range of about 0.002 to about 1.0 mg/kg, more usually from about 0.008 to 0.5 mg/kg, and as for example between 0.015 and 0.15 mg/kg of body weight. In some instances dosage levels below the lower limit of the aforesaid range may be more than adequate, while in other cases still larger doses may be employed without causing any harmful side effect, and therefore the above dosage ranges are not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

I claim:
1. A compound of the formula

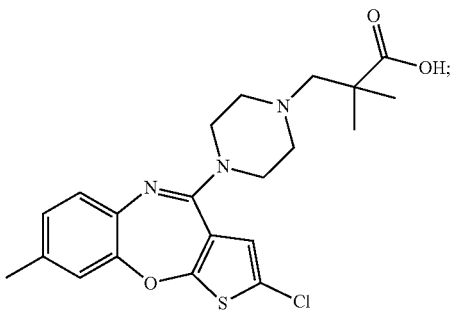 [SMILES: Cc1ccc2c(c1)Oc1sc(Cl)cc1C(N1CCN(CC(C)(C)C(=O)O)CC1)=N2]

or a pharmaceutically acceptable salt thereof.

2. A compound according to claim 1 which is an HCl salt.

3. A pharmaceutical composition comprising a compound of the formula

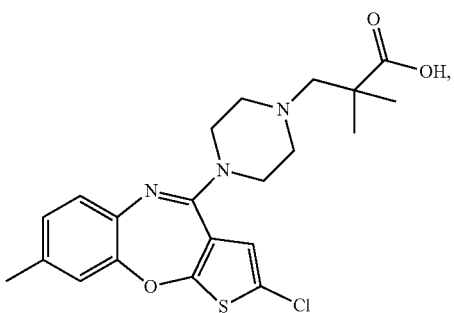 [SMILES: Cc1ccc2c(c1)Oc1sc(Cl)cc1C(N1CCN(CC(C)(C)C(=O)O)CC1)=N2]

or a pharmaceutically acceptable salt thereof, in combination with at least one pharmaceutically acceptable carrier, diluent, or excipient.

4. A method of treating insomnia in a mammal comprising administering to a mammal in need of such treatment an effective amount of a compound of the formula

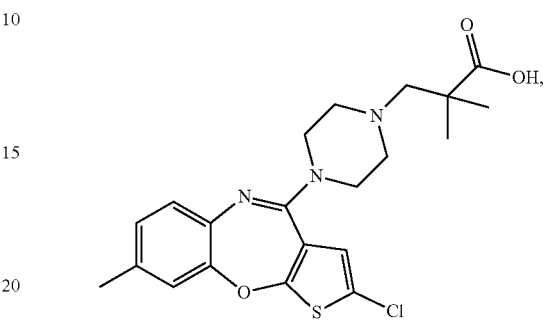

or a pharmaceutically acceptable salt thereof.

5. The method of claim 4 where the mammal is a human.

6. The method of claim 4 where the insomnia is characterized by difficulties in sleep onset or sleep maintenance or both.

7. The method of claim 6 where the mammal is a human.

* * * * *